United States Patent [19]

Miller et al.

[11] 4,157,087
[45] Jun. 5, 1979

[54] PERIPHERAL NERVE STIMULATOR

[75] Inventors: Curtis H. Miller, Burnsville; Mark R. Kaldun, St. Paul, both of Minn.

[73] Assignee: Med General, Inc., Minneapolis, Minn.

[21] Appl. No.: 883,530

[22] Filed: Mar. 6, 1978

[51] Int. Cl.² .......................................... A61N 1/36
[52] U.S. Cl. ................................ 128/741; 128/422; 128/423 R
[58] Field of Search .............. 128/2.1 R, 421, 422, 128/423

[56] References Cited

U.S. PATENT DOCUMENTS

| 2,764,683 | 9/1956 | Paust et al. | 128/423 |
| 3,518,997 | 7/1970 | Sessions | 128/422 |
| 3,612,041 | 10/1971 | Ragsdale | 128/2.06 A |
| 3,612,600 | 10/1971 | Colyer | 128/422 |
| 3,646,940 | 3/1972 | Timm et al. | 128/421 |
| 3,718,132 | 2/1973 | Holt et al. | 128/421 |
| 4,014,347 | 3/1977 | Halleck et al. | 128/422 |

Primary Examiner—William E. Kamm
Attorney, Agent, or Firm—Orrin M. Haugen; Thomas J. Nikolai

[57] ABSTRACT

An electronic peripheral nerve stimulator which may be used to monitor the type of neuromuscular blocks present in a patient following the administration of a muscle relaxant drug. An integrated circuit monostable multivibrator or one-shot is coupled to an amplifier and output stage. Plural integrated astable multivibrators are provided which may be selectively employed to trigger the one-shot circuit to thereby produce stimulating impulses of several predetermined repetition rates and duty cycles useful for producing the so-called "twitch" and "tetanus" responses of a patient's digital members. The peripheral nerve stimulator also includes indicating means for the power-on condition of the unit as well as for a low battery charged condition.

3 Claims, 6 Drawing Figures

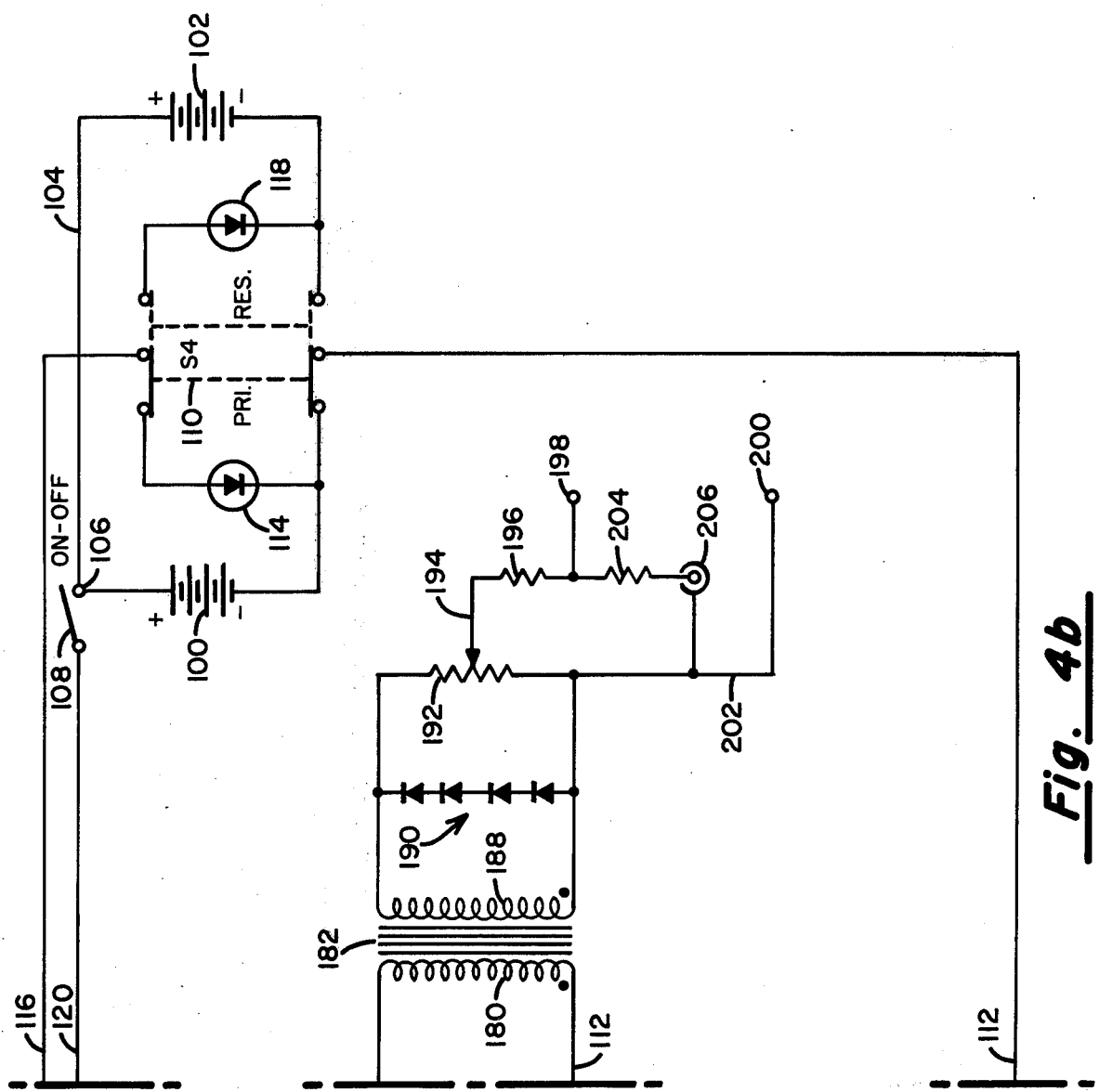

PERIPHERAL NERVE STIMULATOR

BACKGROUND OF THE INVENTION

I. Field of the Invention

This invention relates generally to an electronic nerve stimulating device and more particularly to the improved design of a peripheral nerve stimulator useful in monitoring the nature of neurological blocks present in a patient following the administration of muscle relaxant drugs to the patient.

II. Description of the Prior Art

As is disclosed in the Ide et al U.S. Pat. No. 3,364,929, prior to surgery it is a common practice to administer muscle relaxant drugs such as succinylcholine and dimethyl tubocurare to the patient. Such drugs are found to produce depolarization or non-depolarization types of neuromuscular blocks in patients. Oftentimes, following surgery, it is desired that an antagonist drug be administered to counteract the effects of the muscle relaxant drug previously administered. It is also known that the antagonist drug should be introduced into the patient only when a non-depolarizing block exists in that the introduction of an antagonist drug when a depolarizing block is present is found to potentiate the depolarizing block rather than counteracting the muscle relaxant drug.

As is further set out in the Ide et al U.S. Pat. No. 3,364,929 and the Ide U.S. Pat. No. 3,565,080, the type of block extant within the patient, i.e., depolarizing or non-depolarizing, can be determined by applying electrical stimulation to a peripheral member of the body of the patient and noting the effect of that stimulation on the patient's digits. For example, if electrical pulses of a relatively low repetition rate are applied to the ulnar nerve, a characteristic twitch may be observed in the fingers of the patient. If a stimulation signal of a higher repetition rate is applied to the ulnar nerve, the fingers exhibit a constant contraction called tetanus. If, following the application of the relatively high frequency stimulating pulses, the relatively low frequency pulses are again applied, two different types of twitch reaction take place depending upon whether the patient is exhibiting a non-depolarizing block or a depolarizing block.

Objective evaluation of muscle relaxation during surgery is possible only by indirect stimulation of a skeletal muscle by means of a peripheral nerve stimulator. Most frequently, the ulner nerve is electrically stimulated and the resulting contraction of the hand muscles, i.e., twitching of the fingers is observed. This direct observation of the finger twitches induced by a nerve stimulator provides valuable information (a) on the actual magnitude of neuromuscular blockade (b) on the development of a dual block following suxanethonium, (c) on the need for more muscle relaxant, (d) on the reversal of muscle paralysis by a cholinesterase inhibiting agent, and finally (e) on the differential disagnosis of prolonged postoperative aponea. By employing a nerve stimulator, the neuromuscular blocking agents can be titrated according to the surgical requirements and overdosage can be avoided. By making use of the peripheral nerve stimulator of the present invention, the clinical judgment of muscle relaxation by the anaesthesiologist can be accompanied by a more quantitative and objective evaluation.

In a paper entitled "train-of-Four Nerve Stimulation in the Management of Prolonged Neuromuscular Blockade following Succinylcholine" which was published in the January 1975 issue of *Anesthesiology*, the authors, J. Savarese et al, reported on the value of the response evoked when nerve stimulating pulses were applied in groups of four and at a frequency of approximately 2 Hz. Similarly, in the October 1972 issue of *Anesthesiology*, there appeared a paper by B. Waud et al entitled "The Relation Between the Response to "Train-of-Four" Stimulation and Receptor Occlusion During Competitive Neuromuscular Block". Thus, in the field of anesthesiology, a peripheral nerve stimulator which can be selectively made to emit relatively high frequency tetanizing pulses, relatively low frequency twitch pulses and Train-of-Four pulse patterns is a useful and valuable tool.

SUMMARY OF THE INVENTION

In accordance with the present invention, there is provided a peripheral nerve stimulator which incorporates in a single unit the necessary electronic circuitry for allowing the user to selectively generate twitch pulses at a predetermined low frequency, tetanizing pulses at a relatively higher frequency and Train-of-Four pulse patterns. Controls are also provided in the unit for adjusting the amplitude of the pulses and for accommodating either surface electrodes or percutaneous electrodes. The unit of the present invention further includes suitable indicator means for informing the user as to the particular pulse frequency or pattern being emitted at any given time. Furthermore, the unit is provided with a primary and a reserve battery source and further indicator means are included to advise the user as to the charge condition of the particular source. A switch is provided for disconnecting the primary battery source from the stimulating pulse generating circuits when the potential available from the primary battery falls below a predetermined threshold and for connecting in the reserve battery.

More particularly, the peripheral nerve stimulator of the present invention includes a source of direct current potential, a monostable multivibrator which is connected to be energized by the potential source for producing an output pulse of a predetermined duration each time the monostable multivibrator is triggered. Further included is a plurality of astable multivibrators which are adapted to be individually connected through manually operable switching means to the same source of direct current potential which is used to energize the aforementioned monostable multivibrator. Each of the astable multivibrators, when energized, produces output pulses of predetermined differing frequencies. Means are provided for coupling the outputs of these astable multivibrators to the trigger input terminal of the monostable multivibrator. Furthermore, the peripheral nerve stimulator includes an output means which is responsive to signals developed at the output terminal of the monostable multivibrator for generating constant current stimulating pulses of a desired frequency, rate and amplitude for application to the patient. One of the plurality of astable multivibrators produces pulses at a relatively low frequency rate corresponding to the desired twitch pulse frequency. A second astable multivibrator is designed to operate at a substantially higher frequency so as to provide the tetanizing burst which is found useful in assessing the neuromuscular block extant in the patient. A third astable multivibrator, controlled by its own monostable multivibrator, is used to generate the Train-of-Four pulse pattern.

All of the electronic components are encased in a small, portable and rugged housing. This housing is provided with various alphanumeric information and electronic indicators to facilitate ease and accuracy of use.

OBJECTS

It is accordingly the principal object of the present invention to provide a new and improved peripheral nerve stimulator useful for monitoring the nature of neurological blocks present in a patient following the administration of muscle relaxant drugs to the patient.

Another object of the invention is to provide a unitary peripheral nerve stimulator which can be made to generate a variety of desired pulse patterns.

Still another object of the invention is to provide, in a single unit, a peripheral nerve stimulator for evoking twitch response, tetanus response and for producing Train-of-Four pulse patterns.

A yet further object of the invention is to provide a peripheral nerve stimulator which is easy to use and operates reliably over extended periods of time.

These and other objects and advantages of the invention will become apparent from the following detailed description of the preferred embodiment when considered in light of the accompanying drawings.

DESCRIPTION OF THE DRAWINGS

FIGS. 4a and 4b, when oriented as shown in FIG. 4, depict an electrical schematic diagram showing the implementation of the peripheral nerve stimulator of the present invention.

DESCRIPTION OF THE PREFERRED EMBODIMENT

Figure 1:
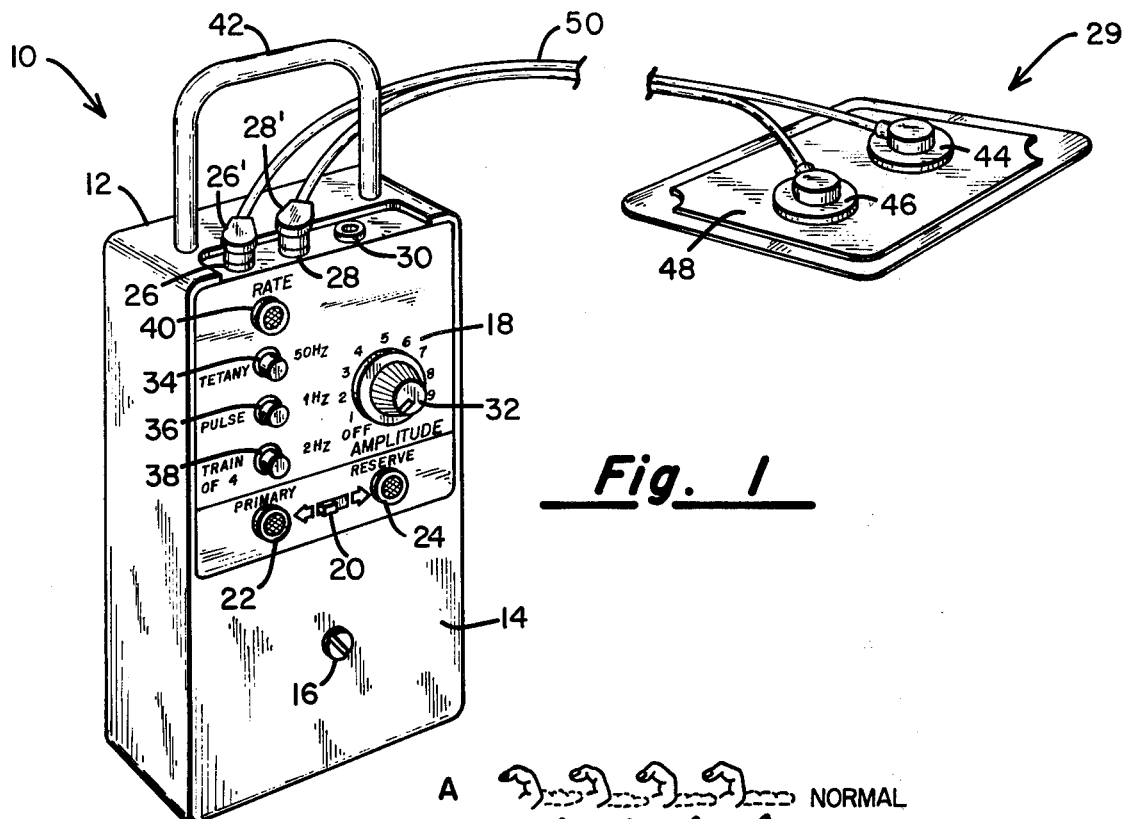
FIG. 1 is a perspective view showing the mechanical features of the preferred embodiment and the various control elements.

Referring first to FIG. 1, there is shown the mechanical design and packaging of the peripheral nerve stimulator of this invention. The electronic circuitry is housed in a generally rectangular case indicated generally by numeral 10, which is preferably fabricated from a suitable high impact resistant plastic material. The case includes a rear enclosure member 12 which includes integrally formed, spaced apart, perpendicularly extending side and end walls. Completing the enclosure is a removable front panel 14 which is preferably fastened to the back member 12 by a large, coin-slotted screw 16. By loosening the screw 16, the cover can be removed for replacement of the battery power source utilized in the device.

Also shown in the drawing of FIG. 1 is a control panel 18 which in the preferred embodiment is formed from aluminum and which has a sheet of Mylar material laminated thereon. The Mylar sheet is imprinted with alphanumeric characters for facilitating the use of the device by medical personnel. Stated otherwise, the alphnumeric information is associated with various control knobs, switches and indicators. More specifically, located at the bottom of the control panel is a slide switch 20 which when disposed in a first position causes a first or primary battery supply to be coupled into the electronic circuitry. When the switch 20 is moved to its opposite position, the "reserve" battery is utilized. Located to the left of the switch 20 is an indicator light labeled "primary". When the switch 20 is in its leftmost position, the primary indicator light 22 is illuminated. Further, as will be explained more fully hereinbelow, when the potential of the primary battery drops below a predetermined threshold, the indicator light 22 will blink on and off to indicate this condition. Similarly, when the switch 20 is in its rightmost position, the indicator 24 labeled "reserve" will glow when the back-up battery is in use. Again, the indicator 24 will blink on and off in the event that the potential of the back-up battery is below a predetermined threshold.

Located on the top of the casing 10 are three electrical jacks 26, 28 and 30. The jacks 26 and 28 are adapted to receive pin connectors 26' and 28', which are associated with surface electrodes 29 when surface electrodes are employed to apply the stimulating impulses to the body of the patient. Jack 30 is a coaxial jack adapted to receive a coaxial pin type connector associated with percutaneous electrodes when that type of electrode structure is employed.

The control knob 32 is used to operate an on-off switch as well as to determine the magnitude of the current available at the output jack. More specifically, when surface electrodes are coupled to the jacks 26 and 28, the control knob 32 may be rotated to vary the peak current between 0 and 30 milliamperes. However, when percutaneous electrodes are coupled to the jack 30, the control knob 32 allows a peak output current of between 0 and 1.5 milliamperes.

Referring now to the left side of the control panel 18, there are shown three push button switches 34, 36 and 38 and an indicator light 40. Again, as will be described fully when the details of the electrical circuitry are explained, depression of the push button switch 34 causes stimulating output signals to be produced at a rate of 50 Hz which is the tetantizing train. However, when the push button 36 is depressed, output signals are produced at a frequency of 1 Hz for so long as the button is held down. Depression of the push button 38 generates a single burst of four stimulating pulses at 0.5 second intervals corresponding to a frequency of 2 Hz. The "rate" indicator 40 flashes once for each output pulse that is produced.

While not critical, the dimensions of the casing 10 may be 14 cm long, by 8.1 cm wide, by 3.9 cm thick. A handle 42, which is generally U-shaped, is attached to the top of the casing 10 and provides a convenient way for supporting or attaching the peripheral nerve stimulator to an equipment stand utilized by the anesthesiologist.

The surface electrodes 29 shown in FIG. 1 generally comprise first and second spaced apart metallic electrodes which are recessed within the compartments 44 and 46 supported by a backing layer 48. The undersurface of the backing layer 48 has a suitable adhesive thereon to facilitate the attachment of the flexible electrode structure to the body of the patient. A jelled sponge is disposed between the skin of the patient and the conductive elements of the electrode to thereby ensure good ohmic contact. The spaced apart metallic electrodes contained within the compartments 44 and 46 are coupled to the surface electrode jacks 26 and 28 of the peripheral nerve stimulator by means of elongated conductors 50.

Figure 2:
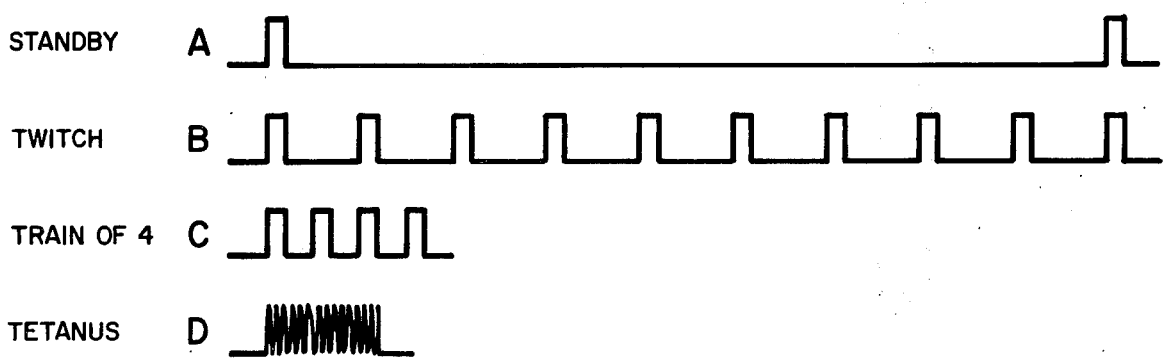
FIG. 2 illustrates the waveforms of the various stimulating impulses produced by the preferred embodiment.

Referring next to FIG. 2, the waveforms of the output signals obtained from the peripheral nerve stimulator of the present invention are illustrated. Waveform A illustrates the output when the unit is in its standby mode. That is, when the on-off switch associated with the control knob 32 is turned to its own position, the unit produces an output pulse at a 0.1 Hz rate. When the push button 36 labeled "pulse" is depressed, the stimulating signals represented by waveform B are produced. More specifically, monophasic rectangular pulses of a 200 microsecond duration are produced at a 1.0 Hz rate. Waveform C illustrates the so-called train of four pattern wherein depression of the push button 38 causes a burst of 4 monophasic rectangular pulses to be generated at 0.5 second intervals. Finally, waveform D represents the tetanus pulse frequency obtained when the push button 34 is depressed. The tetanizing pulse frequency is preferably around 50 Hz for optimum operation.

Figure 3:
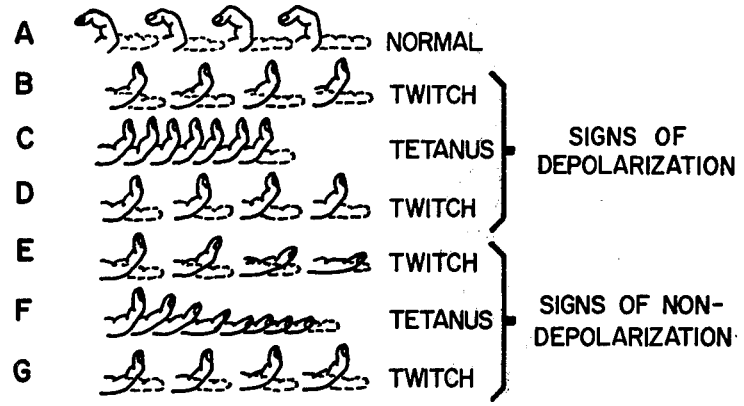
FIG. 3 illustrates the digit response to the waveforms of FIG. 2 when depolarizing and non-depolarizing blocks are present.

With reference to FIG. 3, there is shown the characteristic movements of the fingers in the two classical types of neuromuscular block—depolarization and non-depolarization—when differing pulse patterns are applied to the ulnar nerve. Line A in FIG. 1 illustrates the normal or control response to stimulation when no muscle relaxant drug has been introduced into the patient. Line B illustrates the corresponding response to Train-of-Four stimulation following the administration of succinylcholine as a muscle relaxant. It may be observed that the overall response is not as drastic when compared to the normal response represented by Line A in FIG. 3. Line C illustrates the response when tetanizing pulses are applied. Again, during the duration of the high frequency tetanus burst, the digit remains contracted, but to a lesser extent than the normal response represented by Line A in FIG. 3. Line D of FIG. 3 shows the post-tetanizing response to twitch pulses. The responses depicted by Lines B, C and D are characteristic of depolarization block.

Lines E, F and G in FIG. 3 illustrate characteristic responses where non-depolarization block is extant. The administration of a predetermined dose of tubocurarine is found to precipitate this latter type of response. In Line E, the twitch response to the Train-of-Four stimulation is found to be progressively less upon each successive stimulation pulse in the train. Line F in FIG. 3 shows the response to tetanizing pulse stimulation which is characteristic of non-depolarization block. In Line F it is to be noted that the magnitude of the contraction becomes less and less during the period that the tetanus pulses are applied. Finally, Line G in FIG. 3 shows the twitch response to a Train-of-Four pattern following application of tetanizing pulses.

Based upon the foregoing, then, it can be seen that by monitoring the digit response to various nerve stimulating frequencies and patterns it is possible for a trained anaesthesiologist to characterize the type of neuromuscular block present as well as monitoring the degree of recovery from the application of muscle relaxant drugs and/or antagonist drugs.

Figure 4A:
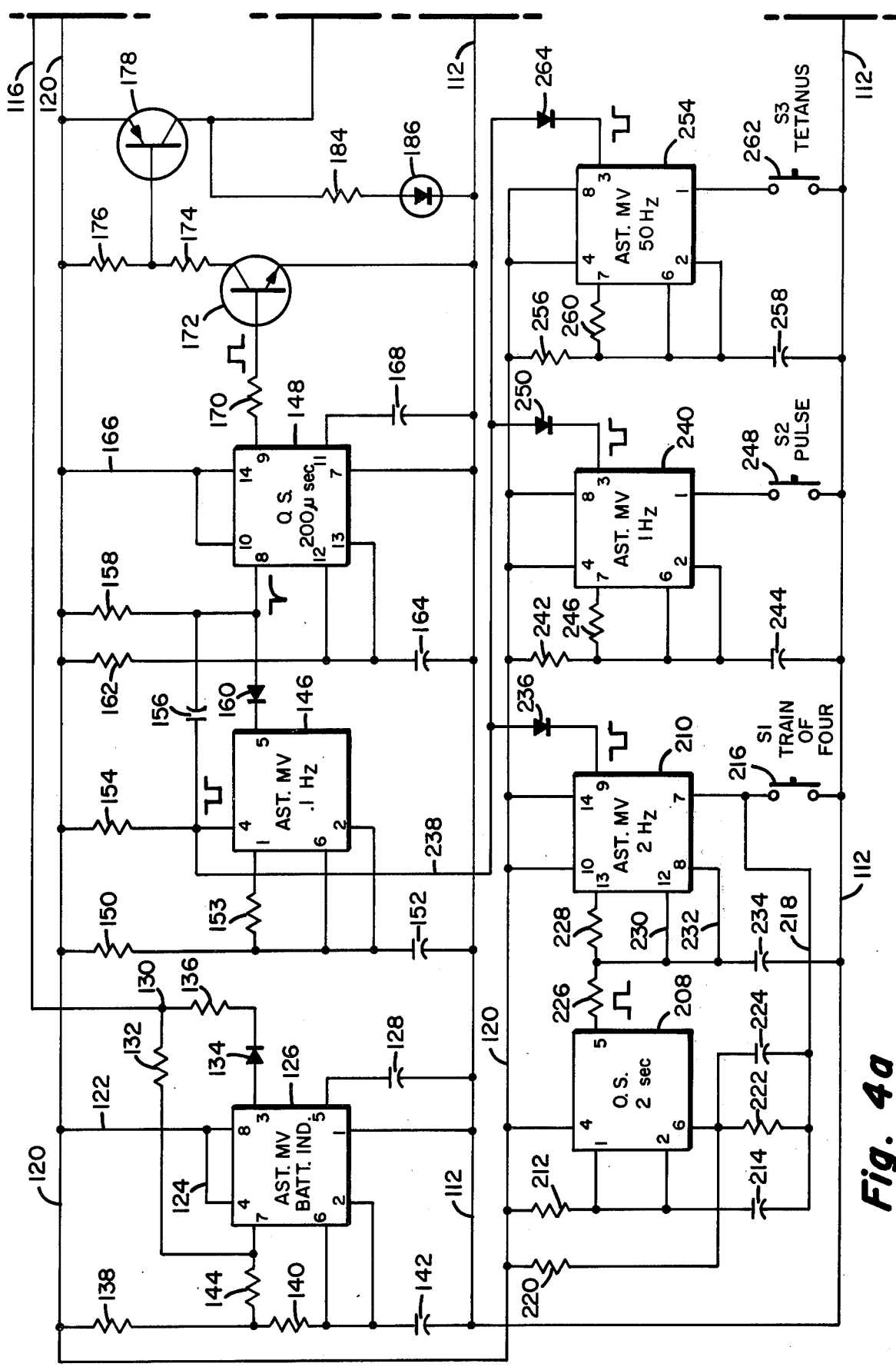

Referring now to FIG. 4, there is shown an electrical schematic diagram of the electronic circuitry used in implementing the peripheral nerve stimulator of the present invention. The circuit is adapted to be energized by a source of direct current potential such as the battery 100. However, an auxiliary or backup DC power source is also provided by way of a second battery 102. The positive terminal of the batteries 100 and 102 are connected in common by means of a conductor 104 and to a first terminal 106 of an on-off switch 108. Which of the two batteries 100 or 102 is operative is determined by the setting of the slide switch 110. The switch 110 is a double pole, double throw arrangement which in its first position connects the negative terminal of the battery 100 to the B- bus 112. A light emitting diode indicator 114 has its cathode electrode also coupled to the negative terminal of the battery 100. The anode terminal of the LED 114 is coupled through the slide switch 110 to a conductor 116. When the slide switch 110 is in the position represented by the dashed line representation in FIG. 4, the negative terminal of the auxiliary battery 102 is connected to the B- bus 112 and the anode electrode of a second LED indicator device 118 is connected to the conductor 116. The cathode of the LED 118 is tied directly to the negative terminal of the battery 102.

When the on-off switch 108 is closed, the $V_{cc}$ bus 120 is connected to the positive terminal of the batteries 100 and 102. When the batteries are fully charged, the voltage on the $V_{cc}$ bus 120 is approximately 9 volts, assuming the batteries are new. This potential is applied by way of conductors 122 and 124 to the $V_{cc}$ terminal and the reset terminal of a type SE555 timer chip 126, i.e., to pins 8 and 4 respectively. The timer chip 126 is connected for astable operation by virtue of the jumper which exists between pins 2 and 6 thereof. Pin 1 of chip 126 is connected to ground and a capacitor 128 is coupled between the B- bus 112 and pin 5 of the integrated circuit. The conductor 116 connects to a junction point 130 and a resistor 132 is coupled between that junction point and pin 7 of the type 555 timer chip 126. The output pin 3 of the chip 126 is coupled through a diode 134 and a resistor 136 to the junction point 130. The external timing circuit for the integrated circuit chip 126 includes the series combination of resistors 138 and 140 with a capacitor 142. The junction point between resistors 138 and 140 is coupled through a resistor 144 to the discharge terminal (pin 7) of the IC chip 126. Pins 2 and 6 of the IC chip 126 are connected to the common point between the resistor 140 and the timing capacitor 142.

By virtue of the interconnections thus far described, the integrated circuit chip 126 will operate in its astable mode. When the battery potential is above a predetermined threshold, e.g., 6 volts, the voltage at output pin 3 stays high causing either LED 114 or LED 118 to glow, depending upon the position of the slide switch 110. As the battery potential drops below approximately 6 volts, the timer chip 126 begins to oscillate, causing either LED 114 and LED 118 to flash and thereby indicate the need to replace the particular battery which is energizing the system at that moment. This low battery condition indicator is achieved by feeding back a voltage to the threshold terminal (pin 6) of the IC chip by way of conductor 116, and resistors 132, 144 and 140. This feedback voltage prevents the potential at pin 6 from reaching $\frac{2}{3} V_{cc}$. When it is understood that the external timing capacitor 142 charges and discharges between $\frac{1}{3}$ and $\frac{2}{3} V_{cc}$ and the voltage must reach $\frac{2}{3} V_{cc}$ in order for the circuit to oscillate, it can be readily seen that a predetermined threshold can be set at which the low battery indicator will flash.

The peripheral nerve stimulator of the present invention is designed to produce an output pulse once every 10 seconds so long as the on-off switch 108 is closed. This is achieved through the use of a type NE556 chip which includes an astable multivibrator 146 and a monostable multivibrator 148 in a single integrated circuit package. The rate of oscillation of the free running multivibrator 146 is determined by the timing circuit which includes the series combination of a resistor 150 and a timing capacitor 152 which is connected between the $V_{cc}$ bus 120 and the B- bus 112. As before, astable operation is achieved by directly connecting the trigger terminal (pin 2) to the threshold terminal (pin 6). The $V_{cc}$ terminal (pin 4) of the astable multivibrator 146 is connected through a resistor 154 to the $V_{cc}$ bus 120. A differentiating circuit including a coupling capacitor 156 and a resistor 158 is connected between the $V_{cc}$ bus 120 and pin 4 of the astable multivibrator 146. The output from circuit 146 is coupled through a diode 160 to the trigger terminal (pin 8) of the monostable multivibrator 148. The period of instability for the one shot circuit 148 is determined by the series combination of resistor 162 and capacitor 164 which are connected in series between the $V_{cc}$ bus and B- bus 112. The common junction between the resistor 162 and the capacitor 164 is connected to both pins 12 and 13 of the dual timer portion 148. Pins 7 and 10 of the integrated circuit 148 are connected directly to the $V_{cc}$ bus 120 by way of a conductor 166. Pin 7 of the integrated circuit 148 is connected directly to the B- bus 112. A capacitor 168 connects the reference terminal, pin 11, of IC 148 to the B- bus 112. The output from the one shot circuit 148 is coupled through a resistor 170 to the base electrode of a NPN transistor 172. The emitter electrode of this transistor is connected to the B- bus and its collector electrode is coupled through series connected resistors 174 and 176 to the $V_{cc}$ bus 120. The common junction between the resistors 174 and 176 is connected to the base electrode of a PNP transistor 178. The emitter electrode of this last mentioned transistor is connected to the $V_{cc}$ bus and the collector electrode is coupled through a parallel circuit which includes the primary winding 180 of an output transformer 182 and the series combination of a resistor 184 and a light emitting diode 186 to the B- bus 112.

The secondary winding 188 of the output transformer 182 has a string of semiconductor diodes indicated generally by numeral 190 connected thereacross and in parallel with a potentiometer 192. The wiper arm 194 of this potentiometer is connected through a first resistor 196 to an output jack 198. The mating jack 200 is connected by means of a conductor 202 directly to one side of the output transformer secondary winding 188. A second resistor 204 is connected between the jack 198 and a coaxial jack 206. The other terminal of the coaxial jack 206 is also connected by the conductor 202 to the terminal of the secondary winding 188.

The values of the resistor 150 and capacitor 152 are set such that the astable multivibrator 146 produces an output signal at a frequency of 0.1 Hz whenever the on-off switch 108 is closed. This signal is coupled through the diode 160 to the trigger terminal of the one shot circuit 148. The resistor 162 and the capacitor 164 are selected such that the one shot circuit 148 has a 200 microsecond period of instability. That is, when a trigger pulse is received at pin 8 thereof, the circuit 148 switches states for a period of 200 microseconds at which time it reverts to its original state. Thus, when the integrated circuit 146 is operative, the circuit 148 will produce a positive going, 200 microsecond square wave pulse every 10 seconds. This positive going pulse, when applied to the base of the transistor amplifier 172 causes its collector electrode to go low which turns on the transistor output stage 178. When transistor 178 turns on, a 9 volt (assuming fully charged battery) 200 microsecond step is applied to the rate indicator 186 and to the primary winding 180 of the output transformer 182. The turn's ratio of the output transformer is such that a 300 volt, 200 microsecond pulse is induced in the secondary winding 188 of the output transformer. Any flyback signal is clipped by the diode string 190. The desired output current is adjusted by means of the potentiometer 192 which is controlled by the knob 32 (FIG. 1). The resistors 196 and 204 in conjunction with the 300 volt open circuit potential developed across the secondary winding of the transformer provides a constant current in the range of from 0 to 30 milliamperes, depending upon the setting of the wiper arm 194. This constant current becomes available at the jacks 198 and 200 which correspond to the jacks 26 and 28 in FIG. 1. The resistor 204 is selected such that the peak current available via the coaxial jack 206 to percutaneous electrodes is in the range of from 0 to 1.5 milliamperes peak.

The "Train-of-Four" pattern of pulses is obtained from the peripheral nerve stimulator of the present invention by means of the type NE556 dual precision timer integrated circuit wihch includes a monostable multivibrator 208 and an astable multivibrator 210. Pin 4 of the monostable circuit 208 is connected to the $V_{cc}$ bus 120 and the period of instability thereof is determined by the RC timing circuit including resistor 212 and capacitor 214. These component values are chosen such that the monostable circuit 208 has a period of instability for 2 seconds. The common junction between the resistor 212 and the capacitor 214 is connected to pins 1 and 2 of the monostable circuit 208. A manually operable push button switch 126 which corresponds to push button switch 38 in FIG. 1, is connected between the B- bus 112 and a conductor 218. Hence, when the switch is closed, the conductor 218 is at the B- potential. The RC timing circuit for the monostable multivibrator 208 is connected between the $V_{cc}$ bus 120 and the conductor 218. Also connected between the $V_{cc}$ bus 120 and the conductor 218 is a series combination of a resistor 220 and a resistor 222. A capacitor 224 is connected directly in parallel with the resistor 222 and the common junction of resistor 220 and resistor 222 is connected to the trigger terminal (pin 6) of the monostable circuit 208. The output from the multivibrator 208 is obtained at pin 5 thereof and is applied to the astable multivibrator 210 by way of a resistor 226. More specifically, the resistor 226 couples the output terminal of monostable circuit 208 to pin 13 of the astable circuit by way of a resistor 228 and to pins 8 and 12 of the astable circuit 210 by way of the conductors 230 and 232. A timing capacitor 234 is coupled between the B- bus 112 and pins 8 and 12 of the astable circuit 210. Pins 10 and 14 of the circuit 210 are connected directly to the $V_{cc}$ bus 120 and pin 7 thereof is adapted to be connected to the B- bus 112 when the push button switch 216 is closed. The output from the astable circuit 210 is obtained at pin 9 thereof and is coupled through a diode 236 to pin 4 of the astable circuit 146 by way of a conductor 238.

In operation, when the "Train-of-Four" push button 216 is closed a current is drawn through the resistive voltage divider which includes resistors 220 and 222 causing a trigger signal to be applied to pin 6 of the monostable circuit 208. This causes the output from the monostable circuit 208 to go high for a period of 2 seconds as determined by the RC time constant provided by the resistor 212 and the capacitor 214. The "high" pulse produced at pin 5 of the monostable circuit 208 enables the astable multivibrator 210 for a 2 second period. Because the timing capacitor 234 and the ohmic value of the resistor 226 are selected to cause the astable circuit 210 to oscillate at a frequency of 2 Hz, exactly 4 pulses will be produced at the output terminal (pin 9) of the astable circuit 210 during the period of instability of the monostable circuit 208. The negative going output pulses appearing at pin 9 of the integrated circuit 210 are coupled through the diode 236 and conductor 238 and are differentiated by the capacitor 156 and the resistor 158 to cause negative going sharp trigger pulses to be applied to pin 8 of the 200 microsecond one-shot circuit 148. The negative going output from the multivibrator 210 also serves to inhibit the 0.1 Hz astable multivibrator 146 and prevents it from affecting the one-shot circuit 148.

The effect of the trigger pulse applied to pin 8 of the 200 microsecond one-shot circuit 148 has already been described. That is, each time one of the 4 trigger pulses is received by the one-shot, its output goes high to turn on transistors 172 and 178. When transistor 178 is turned on, a substantial current is drawn through the primary winding 180 of the output transformer 182 to induce a substantial voltage across its secondary winding 188. It is this voltage that is converted to a constant current by way of the potentiometer 192 and the resistors 196 and 204 to make the stimulating pulses available at the output jacks of the peripheral nerve stimulator. Turning on of transistor 178 also causes the LED indicator 186 to glow and provide a visual indication of the pulse rate.

Following the 2 second period of instability provided by the monostable circuit 208, its output pin 5 goes low which turns off the 2 Hz oscillator 210, ending the pulse train after the 4 pulses have occurred. If the push button 216 is released before all 4 pulses have occurred, the timer circuit 208 resets and is ready to start another pulse train when the push button switch 216 is again depressed.

The peripheral nerve stimulator of the present invention includes a still further integrated circuit precision timer 240 which may be a type NE555 integrated circuit manufactured and sold by the Signetics Corporation. As can be seen from FIG. 4, the integrated circuit 240 is connected up to function as an astable multivibrator. More specifically, pins 2 and 6 thereof are connected together and a RC timing circuit including the resistor 242 and the capacitor 244 are connected between the $V_{cc}$ bus 120 and the B- bus 112. The common junction between the resistor 242 and the capacitor 244 is coupled to pin 7 of the IC chip 240 by way of a resistor 246. Pins 4 and 8 of the chip are tied directly to the $V_{cc}$ bus and pin 1 thereof is adapted to be connected directly to the B- bus 112 by way of a push button switch 248. The component values of the resistor 242 and the capacitor 244 are selected such that the integrated circuit 240 will oscillate at a rate of 1 Hz so long as the push button switch 248 is held closed. The resulting negative going output which appears at pin 3 of the IC circuit 240 is coupled by way of a diode 250 and the conductor 238 to the input of the differentiating circuit which includes the capacitor 156 and the resistor 158. As such, the negative going output pulses produced by the astable multivibrator 240 form trigger pulses for the 200 microsecond one-shot circuit 148. Hence, so long as the "Pulse" push button switch 248 (which corresponds to switch 36 in FIG. 1) is held depressed, the one-shot circuit 148 will produce 200 microsecond duration pulses at a repetition rate of 1 pulse per second. These pulses operate through the transistor amplifiers 172 and 178 and the output transformer 182 in the manner already described.

In order to generate tetanizing pulses, the peripheral nerve stimulator of the present invention includes a still further type NE555 precision timer integrated circuit which is identified by numeral 252 in FIG. 4. This integrated circuit is also connected to function as an astable multivibrator. That is, pins 2 and 6 thereof are jumpered together and a RC timing circuit including the resistor 256 and the capacitor 258 is coupled between the $V_{cc}$ bus 120 and the B- bus 122. The common junction between these two components is coupled by way of a resistor 260 to pin 7 of the integrated circuit chip 254. Pins 4 and 8 of the chip are connected directly to the bus 120. Pin 1 of the astable multivibrator chip 254 is adapted to be coupled through a normally open push button switch 262 to the negative bus 112. The component values of the resistors 256 and 260 and the capacitor 258 are such that the astable multivibrator 254 operates at a 50 Hz rate. The negative going pulses produced by this circuit are obtained at pin 3 thereof and are coupled through the diode 264 and the conductor 238 to the differentiating circuit associated with the trigger input terminal (pin 8) of the 200 microsecond one-shot circuit 148. It can be seen, then, that so long as the Tetanus switch 262 is held depressed, the integrated circuit astable multivibrator 254 will be energized and will produce negative going output pulses at the 50 Hz rate. Each time a pulse is produced at the output of the multivibrator 254, the monostable circuit 148 will be triggered, causing it to generate positive going pulses of a 200 microsecond duration. Again, the positive going output pulses from the monostable circuit 148 turn on the transistors 172 and 178 to develop a substantial output voltage across the secondary winding 188 of the output transformer 182.

Summarizing the operation, then, so long as the on-off switch 108 is closed and the battery potential exceeds a predetermined threshold, e.g., 6 volts, one of the light emitting diodes 114 or 118 will glow to indicate that either the primary battery 100 or the reserve battery 102 (depending upon the setting of the slide switch 110) is adequately charged. However, if the battery in question is not producing a voltage exceeding the pre-established threshold, the astable multivibrator 126 will oscillate and will cause the particular light emitting diode 114 or 118 to blink.

If none of the push button switches 216, 248 or 262 are depressed, the 0.1 Hz astable multivibrator 146 will function to produce an output trigger signal once every 10 seconds to the 200 microsecond one-shot circuit 148. This is the so-called "standby" condition in which stimulating pulses are produced at the output jacks 198-200 or 206 at the 0.1 Hz rate.

When the Train-of-Four switch 216 is closed, the dual timer which includes the monostable circuit 208 and the astable circuit 210 will be energized and the astable circuit 210 will produce exactly 4 output pulses during the period of instability of the monostable circuit 208. These 4 output pulses are used to deactivate the standby oscillator 146 and to activate the 200 microsecond one-shot 148. As a result, each time that the push button switch 216 is depressed, 4 nerve stimulating pulses will be produced at the output jacks.

Depression of the push button switch 248 causes the integrated circuit 240 to be coupled across the supply lines and because of the component values of the timing circuit used therewith, the circuit 240 will produce output pulses at a 1 per second rate for so long as the push button switch 248 is held depressed. The resulting negative going output pulses from the circuit 240 are applied by way of a differentiating network to the trigger input terminal of the 200 microsecond one-shot 148. As a result, the transistors 172 and 178 will be turned on for the duration of the 200 microsecond pulses and will cause a substantial voltage to be developed across the secondary winding 188 of the output transformer 182. Each time a pulse is produced, the light emitting diode 186 will blink to give an indication of the pulse rate then being generated.

In order for the peripheral nerve stimulator of the present invention to produce the so-called tetanizing pulse frequency, an astable multivibrator 254 is provided which becomes energized when the push button switch 262 is closed. The component values for the timing circuit which includes resistor 256 and capacitor 258 are such that the integrated circuit 254 will produce negative going output signals at its output terminal at a 50 Hz rate. These negative going pulses are coupled through the diode 264 and the differentiating circuit of resistor 158 and capacitor 156 to the trigger input terminal of the 200 microsecond one-shot circuit 148. As a result, the transistor switches 172 and 178 will be rendered conductive 50 times per second for a duration of approximately 200 microseconds. When transistor 178 is turned on, a substantial current is made to flow through the primary winding 180 of the output transformer 182 to induce a substantial voltage across its secondary winding 188. The diode string 190 clips off any flyback transients such that monophasic rectangular pulses of a 200 microsecond duration are developed at the output jacks 198–200 or 206 at the 50 Hz rate.

With no limitation intended, typical component values which may be used in implementing the peripheral nerve stimulator of the present invention are set forth below. It is to be understood, however, that other component values may be used since there is a range of stimulating pulse frequencies which may be employed in monitoring the type of neurological block existing in a patient. That is, it is not essential that the twitch pulses be produced at exactly a 1 per second rate nor is it required that the tetanizing pulses be produced at exactly a 50 Hz rate.

TABLE I

| | |
|---|---|
| Batteries 100, 102 | 9V, mallory Duracell MN 1604 |
| LED's 114, 118, 186 | Type FLV110 |
| Diodes 190 | Type 1N914 |
| Diodes 134, 160, 236, 250, 264 | Type 1N914 |
| R138 | 10K ohms |
| R144 | 2.2K ohms |
| R140 | 2.2M ohms |
| R132 | 7.5K ohms |
| R136 | 470 ohms |
| R150 | 6.8M ohms |
| R153 | 47 ohms |
| R154 | 22K ohms |
| R162 | 1.8K ohms |
| R158 | 22K ohms |
| R170 | 1K ohms |
| R176 | 47 ohms |
| R174 | 47 ohms |
| R184 | 47 ohms |
| R196 | 6.2K ohms |
| R204 | 330K ohms |
| R220 | 22K ohms |
| R212 | 680K ohms |
| R222 | 220K ohms |
| R226 | 1.2M ohms |
| R228 | 47 ohms |
| R246 | 47 ohms |
| R256 | 15K ohms |
| R260 | 47 ohms |
| Potentiometer 192 | 10K variable |
| C142 | .033 μf |
| C128 | .01 μf |
| C152 | 2.2 μf |
| C164 | .1 μf |
| C168 | .01 μf |
| C214 | 2.2 μf |
| C224 | .1 μf |
| C234 | .47 μf |
| C244 | 2.2 μf |
| C258 | 2.2 μf |
| IC126 | Type NE555 |
| IC146, 148 | Type NE556 |
| IC208, 210 | Type NE556 |
| IC240 | Type NE555 |
| IC254 | Type NE555 |

There has been thus shown and described a new and improved peripheral nerve stimulator for use in monitoring the neuromuscular condition of a patient who may have been subjected to the administration of muscle relaxant drugs so that the appropriate time for the administration of an antagonist drug can be determined. It will be apparent to those skilled in the art that various changes and modifications may be made to the preferred embodiment disclosed without departing from the spirit and scope of this invention. Accordingly, the true scope of the invention is to be determined from the following claims.

What is claimed is:

1. A peripheral nerve stimulator for selectively applying different patterns of stimulating pulses to the body of a patient for monitoring the neurological reactions of a patient following the administration of muscle relaxant drugs thereto, comprising:

(a) a source of direct current potential;

(b) a first monostable multivibrator having a trigger input terminal and an output terminal, said first monostable multivibrator being connected to said source of direct current potential for producing an output pulse of a predetermined duration each time said monostable multivibrator receives a trigger pulse at said trigger input terminal;

(c) at least three astable multivibrators adapted to be individually connected through manually operable switching means to said source of direct current potential, a first and a second of such astable multivibrators producing output signals of predetermined differing frequencies when so connected to said source of direct current potential;

(d) a second monostable multivibrator having a trigger input terminal and an output terminal, said second monostable multivibrator being connected to said source of direct current potential for producing an output pulse of a predetermined duration when said manually operated switching means is operated;

(e) means coupling the output of said second monostable multivibrator to the third of said astable multivibrators for enabling said third astable multivibrator only during the unstable period of said second monostable multivibrator;

(f) means coupling the outputs of each of said three astable multivibrators to said trigger input terminal of said first monostable multivibrator;

(g) output means responsive to signals developed at said output terminal of said first monostable multivibrator for generating constant current stimulating pulses of a desired frequency, rate and amplitude; and (h) electrode means for applying said stimulating pulses to a site proximate a predetermined peripheral nerve on the patient such that the reaction of the patient to said stimulating pulses can be visually observed.

2. Apparatus as in claim 1 and further including:

(a) an additional astable multivibrator connected to said source of direct current potential and arranged to produce an oscillating output signal only when said potential fails to exceed a predetermined threshold; and (b) indicator means connected to be energized by said oscillating output signal of said further astable multivibrator.

3. Apparatus as in claim 2 wherein said source of direct current potential includes:

(a) a first battery;

(b) a second battery; and (c) switch means for selectively connecting either said first battery or said second battery to said first and second monostable multivibrator, said first, second and third of said astable multivibrators and to said further astable multivibrator.

* * * * *